US009600911B2

(12) United States Patent
Wang et al.

(10) Patent No.: US 9,600,911 B2
(45) Date of Patent: Mar. 21, 2017

(54) RECONSTRUCTION OF OPTICAL COHERENT TOMOGRAPHY (OCT) IMAGES OF MORPHOLOGICAL FEATURES

(71) Applicants: Suzhou Optoring Technology Co. Ltd., Suzhou (CN); General Photonics Corporation, Chino, CA (US)

(72) Inventors: Longzhi Wang, Suzhou (CN); Zhuo Meng, Suzhou (CN); Haimin Yu, Suzhou (CN); Xiaotian Steve Yao, Diamond Bar, CA (US)

(73) Assignees: General Photonics Corporation, Chino, CA (US); Suzhou Optoring Technology Co. Ltd., Suzhou (CN)

( * ) Notice: Subject to any disclaimer, the term of this patent is extended or adjusted under 35 U.S.C. 154(b) by 172 days.

(21) Appl. No.: 14/294,110

(22) Filed: Jun. 2, 2014

(65) Prior Publication Data
US 2014/0355856 A1 Dec. 4, 2014

Related U.S. Application Data

(60) Provisional application No. 61/830,006, filed on May 31, 2013.

(51) Int. Cl.
*G06T 11/00* (2006.01)
*G01B 9/02* (2006.01)
*A61B 5/00* (2006.01)

(52) U.S. Cl.
CPC ........ *G06T 11/005* (2013.01); *G01B 9/02083* (2013.01); *G01B 9/02091* (2013.01); *A61B 5/0066* (2013.01); *A61B 5/0073* (2013.01)

(58) Field of Classification Search
None
See application file for complete search history.

(56) References Cited

U.S. PATENT DOCUMENTS

| | | | | |
|---|---|---|---|---|
| 7,190,464 B2 * | 3/2007 | Alphonse | ............. | A61B 5/0066 356/479 |
| 7,400,410 B2 * | 7/2008 | Baker | .................. | A61B 3/1005 351/210 |

(Continued)

OTHER PUBLICATIONS

A Sakamoto, M Hangai, N. Yoshimura, "Spectral-Domain Optical Coherence Tomography with Multiple B-Scan Averaging for Enhanced Imaging of Retinal Diseases," Ophthalmology. Jun. 2008;115(6):1071-1078.e7. Epub Dec. 3, 2007.*

(Continued)

*Primary Examiner* — Matthew Bella
*Assistant Examiner* — Soo Shin
(74) *Attorney, Agent, or Firm* — Perkins Coie LLP

(57) ABSTRACT

Imaging devices and processing techniques based on imaging information along the depth direction in an optical coherent tomography (OCT) image are disclosed to enhance observed morphological features. The methods and systems obtain different OCT images of the target object under different reference path lengths, process the different OCT images to obtain a derivative with respect to the signal path length of image information of the different images, and processing the derivative to extract improved image information of the target object. The derivatives may be in a form related to a gradient value of the normalized OCT image intensity, or an attenuation coefficient.

34 Claims, 11 Drawing Sheets

(56) References Cited

U.S. PATENT DOCUMENTS

| | | | |
|---|---|---|---|
| 2004/0109164 A1 | 6/2004 | Horii et al. | |
| 2008/0100612 A1* | 5/2008 | Dastmalchi | G06F 19/321 345/418 |
| 2008/0291463 A1* | 11/2008 | Milner | A61B 1/00096 356/491 |
| 2011/0015505 A1 | 1/2011 | Schurman et al. | |
| 2011/0201924 A1 | 8/2011 | Tearney et al. | |
| 2011/0275931 A1* | 11/2011 | Debuc | A61B 3/102 600/425 |
| 2011/0292400 A1 | 12/2011 | Fleming et al. | |
| 2012/0051611 A1* | 3/2012 | Takama | G06T 7/0083 382/128 |
| 2012/0213423 A1 | 8/2012 | Xu et al. | |

OTHER PUBLICATIONS

M Solomon, Y Liu, M Berezin, S Achilefu, "Optical Imaging in Cancer Research: Basic Principles, Tumor Detection, and Therapeutic Monitoring," Med Princ Prac 2011;20:397-415.*

International Search Report and Written Opinion mailed on Jan. 9, 2015 for International Application No. PCT/US2014/040577, filed Jun. 2, 2014 (9 pages).

Igarashi, T., et al., "The Appearance of Human Skin: A Survey," Foundations and Trends® in Computer Graphics and Vision, 3(1):1-95, Jan. 2007.

Levitz, D., et al., "Determination of optical scattering properties of highly-scattering media in optical coherence tomography images," Optics Express, 12(2):249-259, Jan. 2004.

Sakata, L.M., et al., "Optical coherence tomography of the retina and optic nerve—a review," Clinical & Experimental Ophthalmology, 37(1):90-99, Jan. 2009.

Salomatina, E., et al., "Optical properties of normal and cancerous human skin in the visible and near-infrared spectral range," Journal of Biomedical Optics, 11(6):064026(1-9), Nov./Dec. 2006.

Schmitt, J.M., "Optical Coherence Tomography (OCT): A Review," IEEE Journal of Selected Topics in Quantum Electronics, 5(4):1205-1215, Jul./Aug. 1999.

Schmitt, J.M., et al., "Measurement of optical properties of biological tissues by low-coherence reflectometry," Applied Optics, 32(30):6032-6042, Oct. 1993.

Swanson, E.A., et al., "In vivo retinal imaging by optical coherence tomography," Optics Letters, 18(21):1864-1866, Nov. 1993.

* cited by examiner

FIG. 8A  FIG. 8B

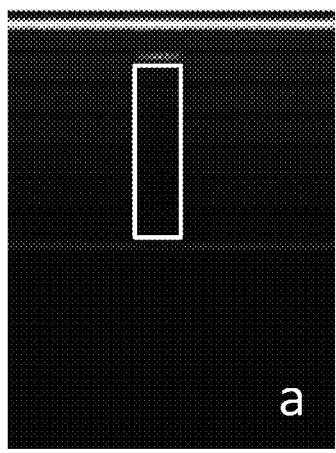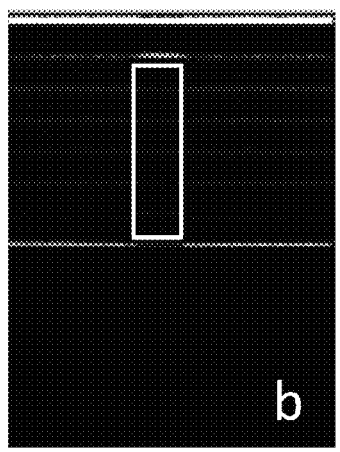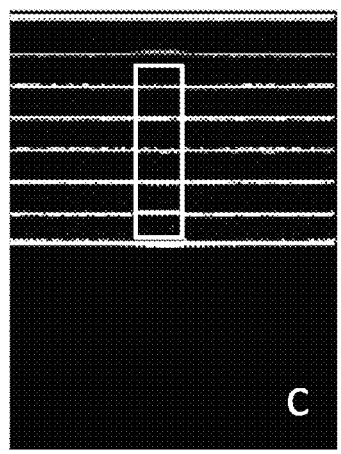
FIG. 11A          FIG. 11B          FIG. 11C
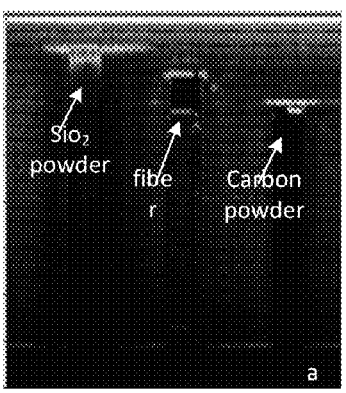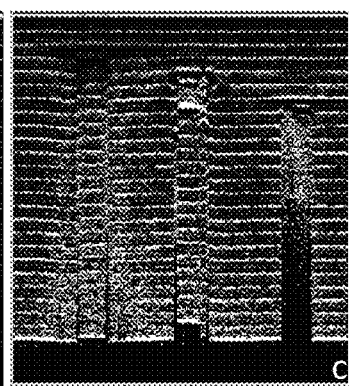
FIG. 12A          FIG. 12B          FIG. 12C

RECONSTRUCTION OF OPTICAL COHERENT TOMOGRAPHY (OCT) IMAGES OF MORPHOLOGICAL FEATURES

PRIORITY CLAIM AND RELATED PATENT APPLICATIONS

This patent document claims the benefit of priority of U.S. Provisional Patent Application No. 61/830,006, filed on May 31, 2013, entitled "ENHANCED RECONSTRUCTION OF OPTICAL COHERENT TOMOGRAPHY (OCT) IMAGES OF MORPHOLOGICAL FEATURES IN DENSE TISSUES." The entire content of the before-mentioned patent application is incorporated by reference as part of the disclosure of this application.

TECHNICAL FIELD

This patent document relates to optical coherence tomography (OCT) devices and methods, including reconstruction of OCT images.

BACKGROUND

Optical coherence tomography (OCT) can be used for non-invasive, optical probing of various substances, including but not limited to, skins, body tissues, and organs of humans and animals. In particular, OCT can be used for sensitively detecting spatial variations of backscattered light inside an object and obtaining its tomographic image with high spatial resolution. For example, OCT is often used in ophthalmology to image the retinal morphological features, since the retina has a clear layered structure and the attenuation of light is weak in retina to allow large penetration depth without degrading signal qualities.

SUMMARY

Techniques and devices disclosed in this document can be used to provide enhanced optical coherence tomography (OCT) images based on slope image information or derivatives of OCT images along the depth direction in OCT images.

The first-order multiple-scattering study indicates that the slope image information along the depth direction in an OCT image can be used to eliminate the effects of signal decay and shadowing, and enhance observed morphological features. OCT slope images have been constructed from original OCT images to demonstrate the advantages, especially the fine-feature enhancement capability of the OCT slope images. Such an image enhancement method can be a powerful tool for various applications, e.g., analyzing the morphological structures in various dense tissues and materials with OCT.

For example, a method is provided for extracting image information from images of a target object in an OCT device obtained via scanning a reference path length relative to a signal path length of a signal path in the interferometer of the OCT device where the target object is located at one end of the signal path. The method may include: obtaining different OCT images of the target object under different reference path lengths, processing the different OCT images to obtain a derivative with respect to the signal path length of image information of the different images, and processing the derivative to extract improved image information of the target object to reduce an effect of a signal decay due to scattering of light in the target object.

For example, a method is provided for extracting image information from images of a target object in an OCT device obtained via scanning a reference path length relative to a signal path length of a signal path in the interferometer of the OCT device where the target object is located at one end of the signal path. The method may include obtaining different OCT images of the target object (1) at different locations shifted in position represented by x and y coordinates along a direction substantially perpendicular to a direction of incidence of light into the target object represented by z coordinate, and (2) at different reference path lengths at each of the different locations to obtain 3-dimensional image information of the target object at the different locations and at different depths with different z coordinates below a surface of the target object; processing OCT images of the target object obtained at different locations shifted in position represented by x and y coordinates to obtain an averaged B-scan image; obtaining a normalized OCT image intensity by dividing a signal intensity of an averaged B-scan image at each position represented by x and y coordinates by a signal intensity at a surface of the target object; obtaining a gradient value of the normalized OCT image intensity with respect to the z coordinate; and using gradient values of the normalized OCT image intensities at different locations to construct an OCT slope image of the target object.

Further refinement of embodiment methods are provided. For example, the method for processing the different OCT images to obtain a derivative with respect to the signal path length of image information of the different images may comprise: averaging a first number of consecutive B-scan images among the different OCT images to obtain an averaged B-scan image; obtaining a normalized OCT image intensity of a position in the averaged B-scan image by dividing a signal intensity of the position in the averaged B-scan image by a signal intensity at a surface of the target object; calculating a gradient value of the normalized OCT image intensity in the signal path length direction by subtracting a normalized OCT image intensity in a next depth to the normalized OCT image intensity; and obtaining the derivative with respect to the signal path length by dividing the gradient value of the normalized OCT image intensity by double actual distance of one pixel.

Further refinement of embodiment methods are provided. For example, the method for processing the different OCT images to obtain a derivative with respect to the signal path length of image information of the different images may comprise: selecting a B-scan image among the different OCT images of the target object under different reference path lengths at different locations shifted in position represented by x and y coordinates; removing noise in the selected B-scan image to obtain a denoised B-scan image; obtaining a normalized OCT image intensity by dividing a signal intensity of the denoised B-scan image at each position represented by x and y coordinates by a signal intensity at a surface of the target object; selecting an A-scan signal of a point at the denoised B-scan image with normalized OCT image intensity; dividing the signal path length into a plurality of smaller segments; selecting data of the A-scan signal in the signal depth direction at a segment containing a depth z; calculating the derivative of the A-scan signal in the segment with the selected data at the segment containing the depth z; and calculating iteratively derivatives of the A-scan signal through all segments in the signal path.

Further refinement of embodiment methods are provided. For example, the method for processing the different OCT images to obtain a derivative with respect to the signal path length of image information of the different images may comprise: averaging a first number of consecutive B-scan images among the different OCT images to obtain an averaged B-scan image; obtaining a normalized OCT image intensity in the averaged B-scan image by dividing a signal intensity of an averaged B-scan image at each position represented by x and y coordinates by a signal intensity at a surface of the target object; obtaining a gradient value of the normalized OCT image intensity in the signal path length direction by subtracting an OCT signal intensity in a next depth to the OCT signal intensity; calculating an attenuation coefficient by dividing the gradient value by double actual distance of one pixel and then multiplying −1; and obtaining an enhanced attenuation coefficient by dividing the attenuation coefficient by the normalized OCT image intensity.

In addition, optical coherence tomography (OCT) devices are disclosed. An embodiment of the OCT device may comprise an optical interferometer and an imaging processing device. The optical interferometer may have a signal path in which a target object is located to receive light of a signal beam and a reference path for carrying a reference light beam to cause a spatial overlap the reflected or back scattered signal light from the target object and the reference light beam to produce an OCT optical signal beam containing different OCT images of the target object that are obtained (1) at different locations shifted in position represented by x and y coordinates along a direction substantially perpendicular to a direction of incidence of light into the target object represented by z coordinates in the signal path, and (2) at different reference path lengths of the reference path at each of the different locations to obtain 3-dimensional image information of the target object at the different locations and at different depths with different z coordinates below a surface of the target object. The imaging processing device may process the OCT images of the target object obtained at different locations shifted in position represented by x and y coordinates to obtain an averaged B-scan image, obtain a normalized OCT image intensity by dividing a signal intensity of an averaged B-scan OCT image at each position represented by x and y coordinates by a signal intensity at a surface of the target object, obtain a gradient value of the normalized OCT image intensity with respect to the z coordinate, and use gradient values of the normalized OCT image intensities at different at different locations to construct an OCT slope image of the target image.

These and other aspects, features and their implementations and variations are described in greater detail in the drawings, the description and the claims.

BRIEF DESCRIPTION OF THE DRAWINGS

FIGS. 8A-8C show an illustration of a procedure for removing noise in an OCT image, and calculating the slope signal to obtain an OCT slope image from the OCT image with noise removed and using curve fitting.

FIGS. 11A-11C, 12A-12C show further exemplary comparisons of the original OCT image and enhanced OCT slope images.

DETAILED DESCRIPTION

This document proposes and demonstrates using an optical coherence tomography (OCT) slop image to enhance the visualization of morphological features of OCT images. Such an OCT slope image can be obtained by taking the derivative of an OCT scan in the signal depth direction known as "A-scan" in the OCT instrumentation field. Based on the first-order multiple-scattering theory, the derivative signal of an OCT image can reduce signal decay in a strong scattering medium, such as a dense tissue. In addition, it has the capability to significantly reduce the shadowing effect and enhance the boundaries of heterogeneous layers. The proposed techniques have been verified in overcoming the signal decay and shadowing effects on demonstrated examples.

Procedures to obtain OCT slope images are shown in details in this document. The procedures can be applied to skin tissues as well as other artifacts and target objects being imaged by an OCT system. As demonstrated with a section of in-vivo human forearm skin, OCT slope images can greatly enhance the visualization of hidden morphological features, especially at depths when the original OCT image cannot show any spatial structures. It is expected that the OCT slope imaging technique will become a powerful tool for the tomographic visualization and identification of morphological structures, even under the influence of noises.

The disclosed technology can be used to enhance OCT image quality. Various undesirable imaging effects can degrade OCT images. For example, when OCT is used in dense tissues, such as a skin, the intensity of the OCT signal quickly decays with the increased penetration depth. In addition, a region in a tissue with strong scattering or attenuation often diminishes the light beneath it and casts a shadow. Although the OCT image of the region itself is clear, such a shadowing effect generally prevents the formation of clear OCT images of morphological features in the shadow. Finally, the strong multiple photon scattering process in dense tissues further smears the details of OCT signal resulting from the structural variations in the tissue, making it difficult to identify fine morphological changes.

Many researches focus on developing methods to quantitatively evaluate the bulk optical properties of a dense tissue in a particular depth range of interest, such as dermis of a skin, instead of on enhancing the visualization of fine morphological features. Because the bulk optical properties are generally extracted with the average values over certain sample volumes to avoid the influence of the heterogeneity of dense biological tissues, they cannot be used to analyze the fine morphology structures.

Methods for analyzing the fine morphology structures and reconstructing OCT images of fine morphology structures are needed. Implementations of the disclosed technology in this document can be used to, among other applications, provide methods and devices in meeting the above need.

Figure 1:
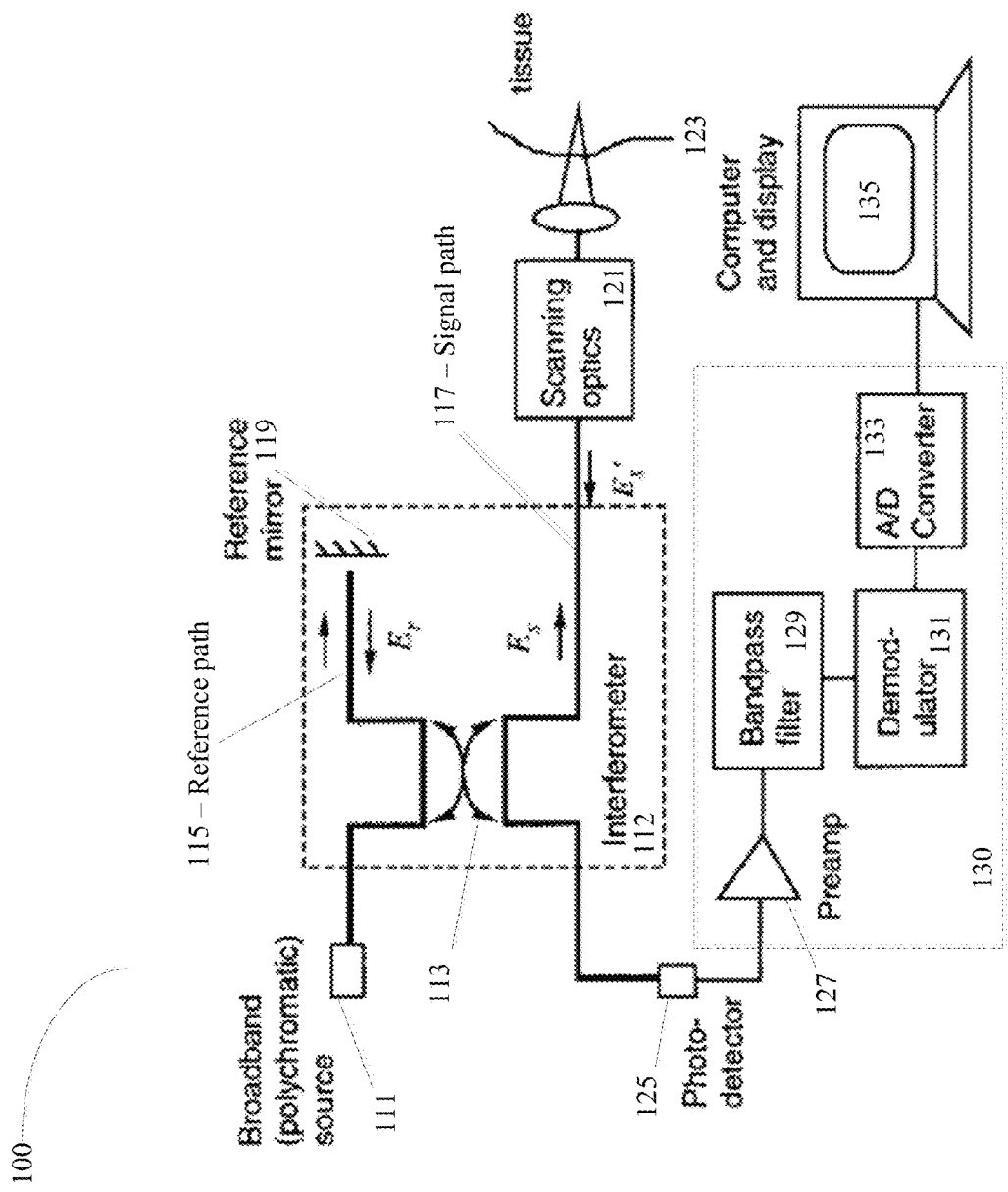
FIG. 1 shows an exemplary optical coherence tomography (OCT) system.

FIG. 1 shows an exemplary OCT system 100. The optical design of the OCT system 100 and its associated features and other OCT technical features are described in Optical Coherence Tomography (OCT): A Review" by Joseph M. Schmitt, in IEEE JOURNAL OF SELECTED TOPICS IN QUANTUM ELECTRONICS, VOL. 5, NO. 4, JULY/AUGUST 1999, p. 1205-1215, which is incorporated by reference in its entirety as part of this document. The main components of the OCT system 100 are an interferometer 112 illuminated by a broadband light source 111. The interferometer 112 includes an optical coupler 113 connected to a reference mirror 119 through a reference path 115, and connected to a scanning optics 121 through a signal path 117. Light passes through the scanning optics 121 to reach the tissue 123 or any other target object 123 placed at the end of the signal path 117.

In the OCT system 100, the light from the light source 111 is split into a sampling beam along the signal path 117 and a reference beam along the reference path 115 which propagate in two separate optical paths, respectively. The light source 111 may be a partially coherent source, e.g., a broadband light source or a polychromatic light source. The sampling beam is directed along its own signal path 117 to impinge on the target object 123 under study, or sample, while the reference beam is directed in a separate reference path 115 towards a reference surface, the reference mirror 119.

The beams reflected from the target object 123 and from the reference mirror 119 are then brought to spatially overlap with each other to optically interfere at or by the optical coupler 113. Because of the wavelength-dependent phase delay the interference results in no observable interference fringes unless the two optical path lengths of the sampling and reference beams are very similar. This provides a physical mechanism for ranging. The optical coupler 113, which may be a beam splitter, may be used to split the light from the light source 111 and to combine the reflected sampling beam and the reflected reference beam for detection at an optical detector 125. This use of the same device, the optical coupler 113, for both splitting and recombining the radiation is essentially based on the well-known Michelson interferometer. The discoveries and the theories of the interference of partially coherent light are summarized by Born and Wolf in "Principles of Optics", Pergamon Press (1980).

The recombined light is directed into the optical detector 125 and the electrical output of the optical detector 125 is directed to a post-detector circuit 130 before being processed by a computing device 135. In the OCT system 100, the post-detector circuit 130 may comprise an amplifier 127, an optional bandpass filter 129, a demodulator 131, and finally an A/D converter 133 which converts an analog signal to a digital signal before it is processed by the computing device 135. Other configurations of the post-detector circuit 130 may be designed and used as well.

Figure 6:
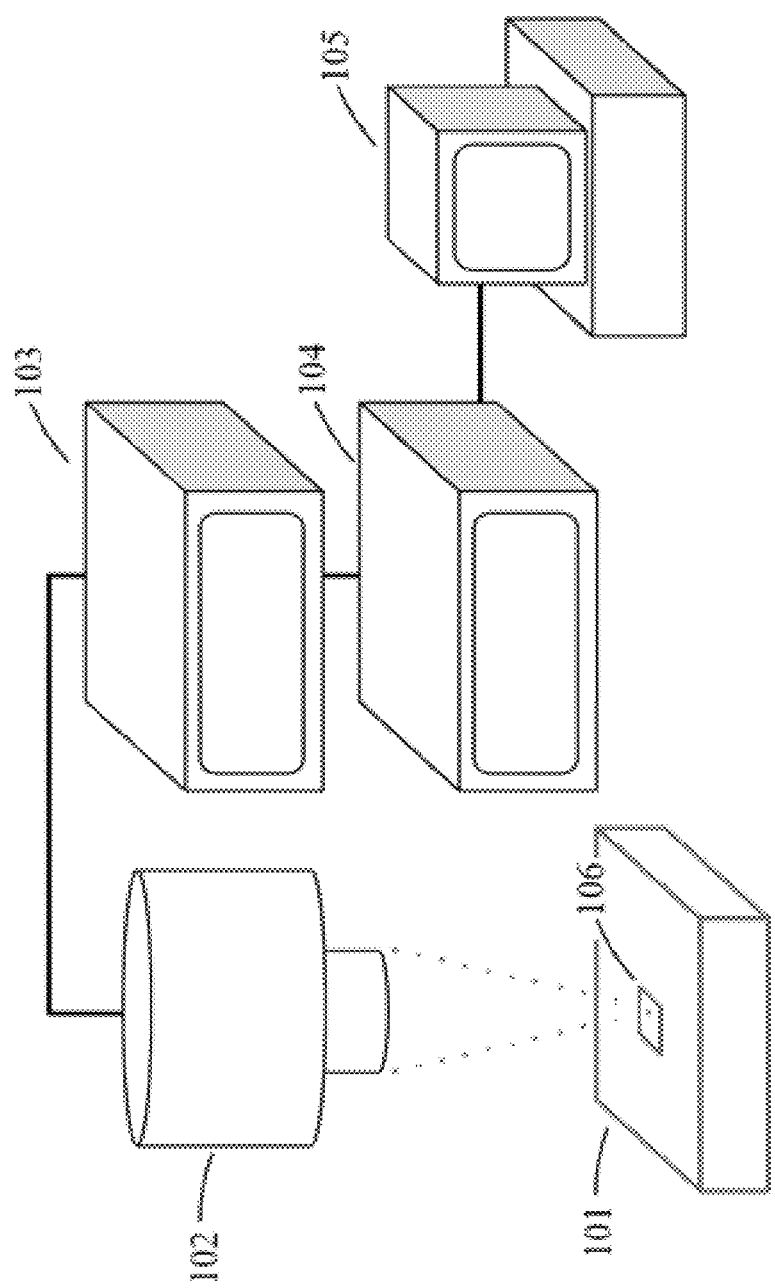
FIG. 6 shows an example of an OCT system that implements the OCT design configuration in FIG. 1 and other OCT design configurations.

The OCT system 100 shown in FIG. 1 is one example. Other OCT configurations may also be used. FIG. 6 shows an example of OCT system that implements the OCT system in FIG. 1 and in other OCT configurations for obtaining OCT images. In this example, the OCT main console (103) controls the scanner (102) to image the sample (101) at the region of 106, and then the OCT image data is transported into the module of data processing (104) to acquire the OCT slope image by the computer (105). As disclosed in the U.S. Provisional Patent Application No. 61/830,006, an OCT system can obtain OCT images at different depths based on spectral interferometry by recording a correlogram with the reference mirror fixed in position. Fourier transformation of the correlogram yields the reflectivity profile of the tissue in the depth dimension.

Figure 2:
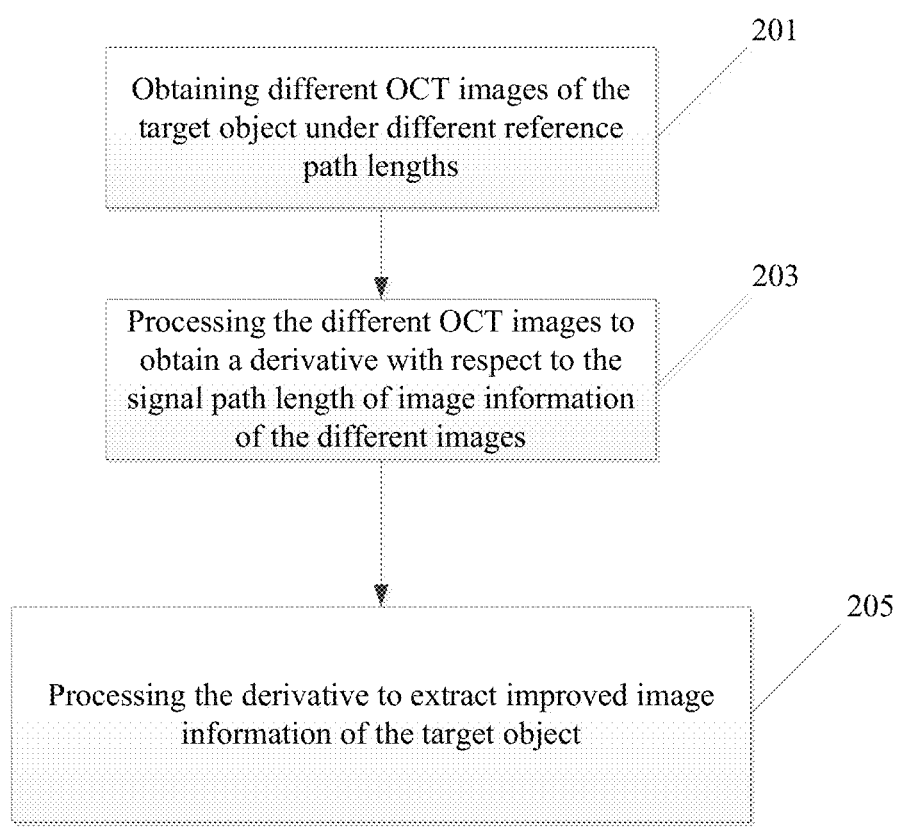
FIGS. 2-4 show exemplary flow charts of methods for obtaining an OCT slope image based on derivatives.

FIG. 2 shows an exemplary flow chart of a method for obtaining an OCT slope image based on derivatives. For example, the method can be applied to the target object 123 placed in the OCT system 100 as shown in FIG. 1. The OCT system 100 may scan the reference path 115 and the signal path 117 in the interferometer 112, where the target object 123 is located at one end of the signal path 117. The method can be applied to other OCT systems as well.

At the step 201, different OCT images of the target object 123 under different reference path 115 lengths may be obtained. The different OCT images may be a part of the 3-dimensional image information of the target object 123 obtained at the different locations and at different depths with different z coordinates below a surface of the target object 123. More details will be shown in different embodiment methods later.

At the step 203, the different OCT images are processed by various methods to obtain a derivative with respect to the signal path length of image information of the different images. The derivatives may have different form, scaled or further processed to a metric related to the derivatives. For example, the derivatives may be calculated in a form of gradient values in an embodiment method shown in FIG. 3. Alternatively, the derivatives may be calculated as slope values which are obtained from the gradient values in an embodiment method shown in FIG. 4. Yet in another alternative, the derivatives may be calculated as attenuation coefficients which are obtained from the gradient values in an embodiment method shown in FIG. 10. These formats of the derivatives and others not listed are within the scope of this document.

At the step 205, the derivatives of the OCT images are further processed to extract improved image information of the target object. As a result of the step 205, an OCT slope image may be constructed with reduced effect of a signal decay due to scattering of light in the target object 123. Alternatively, the OCT slope image may have enhanced image information of boundaries of heterogeneous layers in the target object 123.

A theoretical analysis of OCT imaging is provided below to assist understanding of how an OCT slope image can reduce effect of signal decays, enhance image information of boundaries of heterogeneous layers, and reveal more detailed morphological features.

In the first-order multiple-scattering theory, the OCT A-scan signal in a medium is given by the following equation:

$$P_n(z)=P(z)/P_iA(z)=K\mu_b(z)\exp(-2\mu z) \quad (1)$$

where $P_n(z)$ and $P(z)$ are the normalized OCT signal and un-normalized OCT signal intensities at depth z beneath the light incident surface, respectively, $P_i$ is the OCT signal intensity at the light incident surface, $A(z)$ is the beam divergence function, K is a constant relating to the source coherence function, $\mu_b(z)$ is the backscattering function of the medium at a depth z beneath the surface, which carries the morphological information of the medium, and $\mu_t$ is the attenuation coefficient of the medium and is nearly a constant in a particular depth range, such as the dermis of a skin. The coherence length of the source, the incident power are known, and the divergence function $A(z)$ of the beam is also known and almost a constant.

Therefore, the normalized OCT signal intensity $P_n(z)$ decays exponentially at a rate equal to twice the attenuation coefficient $\mu_t$ of the medium. In a dense medium or tissue, the photon attenuation is so severe such that the morphological details deep in the medium are obscured in an OCT image due to reduced signal to noise ratio.

It should also be noticed that a large $\mu_b(z)$ at a depth z diminishes its values below z. For example, if $\mu_b(z)$ at a depth z is too large due to a strong local scattering, there will be few photons in the regions below, resulting in a small $\mu_b(z)$ and a corresponding obscured OCT image in these regions, and causing a shadowing effect.

Morphological features of a target object in an OCT A-scan can be more clearly identified by detecting the changes of $\mu_b(z)$ along z. Such signal changes can be mathematically obtained by taking the derivative of the original OCT signal. OCT signals are often represented on a logarithmic scale to accommodate signal's large dynamic range. Taking the derivative of the normalized logarithmic OCT signals along z, a different equation is obtained shown below:

$$d\{\ln [P_n(z)]/dz\} = \mu'_b(z)/\mu_b(z) - 2\mu_t \quad (2)$$

where $\mu'_b(z)$ is the derivative of the backscattering function in the z direction and represents its differential changes caused by the morphological structures in the target object.

Eq. (2) shows that the OCT depth derivative signal no longer decays along z and the attenuation coefficient merely contributes a constant background. In addition, the OCT depth derivative signal is only proportional to the relative differential backscattering function $\mu'_b(z)/\mu_b(z)$, a quantity only sensitive to the rate of change for $\mu_b(z)$, not its absolute value.

Because the rate of the OCT signal change is the largest at the boundaries of a target object's morphological structures and smallest inside the structures, the OCT depth derivative signals have an advantageous edge enhancement effect. Moreover, the different signs of the derivative for the increasing and decreasing slopes of the signal can provide additional information about the internal structure in the tissue. Finally, the shadowing effect described previously can also be reduced because $\mu'_b(z)/\mu_b(z)$ does not depend on the absolute value of $\mu_b(z)$. Therefore the image reconstructed by the depth derivative of OCT A-scans can reveal more detailed morphological features inside a dense tissue, such an image may be called an OCT slope image.

Based on the analysis presented above, more detailed embodiment methods are presented in FIGS. 3-4, FIG. 7, and FIG. 10, which can be viewed as refinements of the general method presented in FIG. 2.

Figure 3:
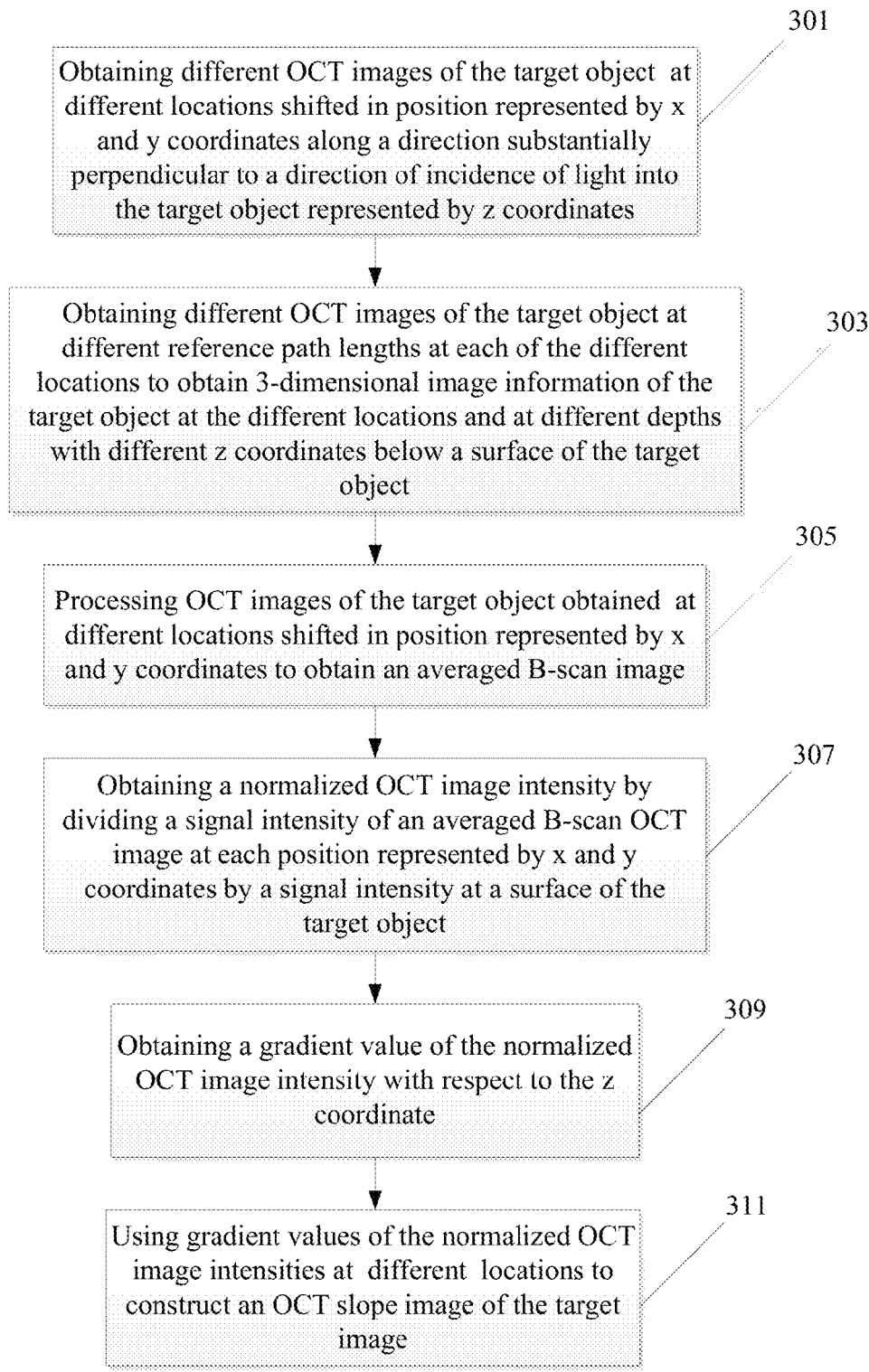

FIG. 3 shows a flow chart of a method for obtaining an OCT slope image based on derivatives. The method can be applied to the target object 123 placed in the OCT system 100 as shown in FIG. 1. The OCT system 100 may scan the reference path 115 and the signal path 117 in the interferometer 112, where the target object 123 is located at one end of the signal path 117. The method can be applied to other OCT systems as well.

At the step 301, different OCT images of the target object 123 at different locations are obtained. The locations are positions represented by x and y coordinates along a direction substantially perpendicular to a direction of incidence of light into the target object 123 represented by z coordinate. In the exemplary OCT system 100 shown in FIG. 1, the z coordinate would be the direction of the signal path 117, and the x and y coordinates are along a direction substantially perpendicular to the signal path 117.

At the step 303, different OCT images of the target object 123 are obtained at different reference path 115 lengths at each of the different locations as identified by the x and y coordinates. As a result of the step 301 and the step 303, 3-dimensional image information of the target object 123 is obtained at different locations and at different depths with different z coordinates below a surface of the target object 123.

At the step 305, the OCT images of the target object 123 obtained at different locations shifted in position represented by x and y coordinates ("B-scan") at the step 301 may be processed to obtain an averaged B-scan image at different z coordinate below a surface of the target object 123. There may be many different ways to obtain the average B-scan image. More details may be shown later in this document.

At the step 307, a normalized OCT image intensity may be obtained by dividing a signal intensity of an averaged B-scan image at each position represented by x and y coordinates by a signal intensity at a surface of the target object 123.

At the step 309, a gradient value of the normalized OCT image intensity with respect to the z coordinate below a surface of the target object is obtained. The gradient value of the normalized OCT image intensity may be viewed as a representation of the derivative as shown by Equation (2) above. In some other methods, more accurate calculation of the derivatives can be further performed based on the gradient values, which will be shown later.

At the step 311, an OCT slope image of the target object may be constructed using gradient values of the normalized OCT image intensities at different locations at a z coordinate below a surface of the target object. The OCT slope image may have reduced effect of a signal decay due to scattering of light in the target object 123. Alternatively, the OCT slope image may have enhanced image information of boundaries of heterogeneous layers in the target object 123.

Figure 4:
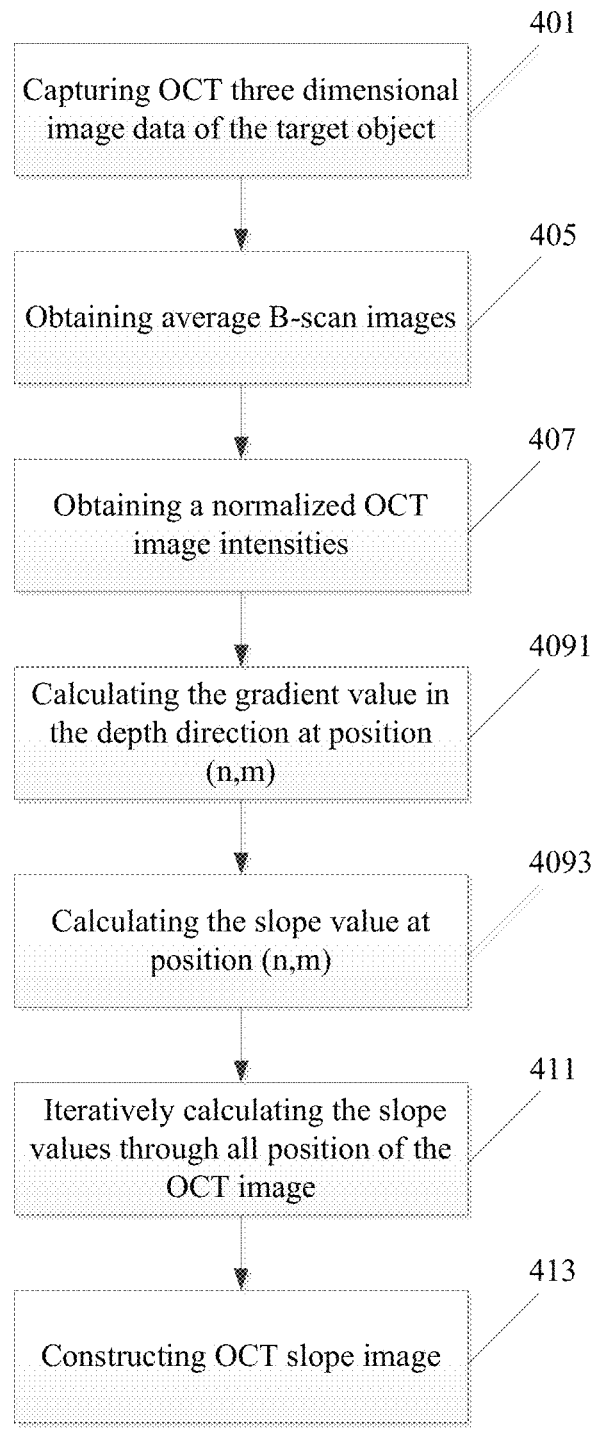

FIG. 4 shows a flow chart of a method for obtaining an OCT slope image based on derivatives. The method can be applied to the target object 123 placed in the OCT system 100 as shown in FIG. 1. The OCT system 100 may scan the reference path 115 and the signal path 117 in the interferometer 112, where the target object 123 is located at one end of the signal path 117. The method can be applied to other OCT systems as well.

At the step 401, 3-dimensional image information of the target object 123 may be captured by the OCT system. The 3-dimensional image information of the target object 123 may be captured by similar steps shown in the step 301 and the step 303 in FIG. 3. For example, 3-dimensional image information of the target object 123 may be obtained at different locations and at different depths with different z coordinates below a surface of the target object 123.

At the step 405, an averaged B-scan image at different z coordinate below a surface of the target object 123 is obtained. For example, the averaged B-scan image may be obtained by averaging 20 consecutive B-scan images to suppress the influence of speckle noise. There may be other number of consecutive B-scan images to be averaged instead of 20. The exact number of consecutive B-scan images to be averaged depends on the OCT system, the target object, and other factors affecting the performance. There may be other ways to remove noises instead of taking an average of consecutive B-scan images.

At the step 407, a normalized OCT image intensity may be obtained by dividing a signal intensity of an averaged B-scan image at each position represented by x and y coordinates by a signal intensity at a surface of the target object 123.

At the step 4091, a gradient value of the normalized OCT image intensity with respect to the z coordinate below a surface of the target object is obtained. The gradient value G(n,m) in the signal depth direction may be obtained by subtracting the OCT signal intensity (in logarithmic scale) in the next depth I(n+1,m) to the OCT signal intensity I(n,m), $G(n,m)=\ln[I_n(n+1,m)]-\ln[I_n(n,m)]$.

At the step 4093, the derivative value, or the slope value $d\{\ln[P_n(z)]/dz\}$ can be obtained by dividing the gradient value G(n,m) by a double actual distance of one pixel, as below: $d\{\ln[P_n(z)]/dz\}=G(n,m)/2\delta z$.

The steps 4091 and 4093 can be viewed as a refinement of the step 309 shown in FIG. 3, where only the calculation of the gradient value is performed. Both methods shown in FIG. 3 and in FIG. 4 are different embodiments of the general method as shown in FIG. 2.

In addition, at the step 411, similar derivatives with respect to the signal path length through all positions of the averaged B-scan image are iteratively calculated.

At the step 413, an OCT slope image having improved image information of the target object is constructed from the derivatives with respect to the signal path length through all positions of the averaged B-scan image.

The method illustrated in FIG. 4 is applied to some example artifact to demonstrate the effectiveness and correctness of the OCT slope images. An artifact is constructed using multiple layers of Scotch® 810 Magic™ tapes to show the heavy scattering effect, with an embedded ink mark on the 4th layer to act as a strong attenuation feature.

Figure 5A:
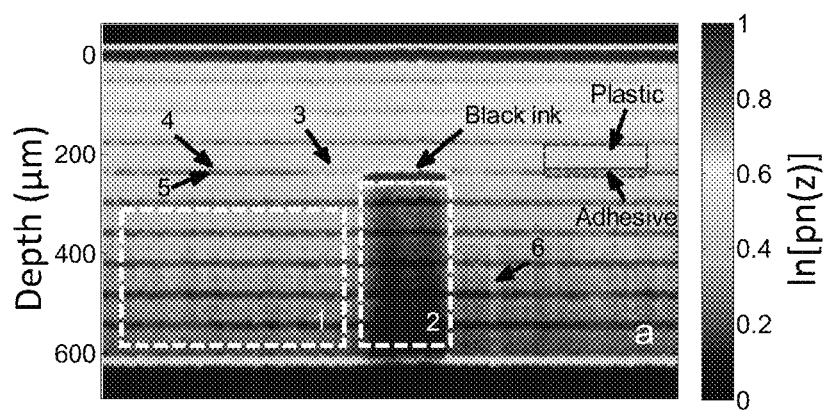
FIGS. 5A-5C show an exemplary comparison of an original OCT image with a corresponding OCT slope image, and a positive OCT slope image for a target object.

FIG. 5A shows an average B-scan image of the above constructed artifact obtained by averaging 20 consecutive B-scan images to suppress the influence of speckle noise. Both the signal decay and shadowing effects are clearly shown in areas marked with 1 and 2. The OCT images are obtained by a swept source OCT system with a central wavelength of 1325 nm, a spectral bandwidth of 100 nm, a transverse resolution of 25 μm and an axial resolution of 12 μm in the air. Each longitudinal A-scan is obtained by averaging four individual A-scans. OCT volume data are acquired with 104 pixels×104 pixels (2.6 mm×2.6 mm) in the lateral direction and 512 pixels (3 mm in air) in the depth direction.

Figure 5B:
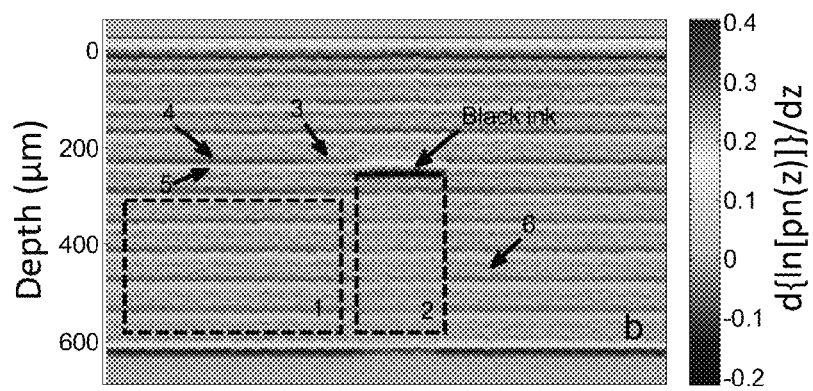

FIG. 5B shows an OCT slope image obtained by taking the depth derivative of each OCT A-scan in FIG. 5A as described in the method shown in FIG. 4. As expected, both the signal decay and shadowing effects in areas 1 and 2 are greatly reduced and the boundaries between the plastic and the adhesive are enhanced. In addition, some less clear features, such as that indicated by arrow 3, become easily distinguishable. Note that there are double lines at each tape boundary marked with arrows 4 and 5, representing the dramatically decreasing and increasing scattering when light passing through the boundary, where the decreasing scattering is evidenced by a negative slope caused by light from high scattering plastic to low scattering adhesive, while the increasing scattering is evidenced by a positive slope caused by light from adhesive to next plastic layer.

Figure 5C:
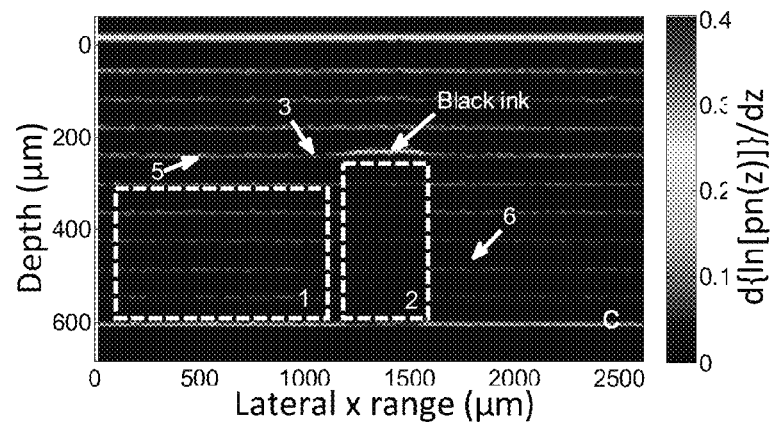

To avoid the visual blur caused by the double lines, only the positive (or negative) value of the derivatives is kept and shown in FIG. 5C. The boundary enhancement effect becomes more apparent, as the signal decay and shadowing effects are effectively reduced. Note that all structural features shown in FIG. 5C are expected from the artifact and no incorrect features are present. It is also interesting to note that the unwanted vertical stripes indicated by arrow 6 in FIG. 5A are effectively removed in FIG. 5B and FIG. 5C.

The method shown in FIG. 4 may be used in obtaining OCT images the artifact made with adhesive tapes, as shown above, or similar things. The artifact is of low scattering and the spatial noise is relatively small. Therefore, the procedure shown in steps from the step 405 to step 4093 may work well for such low scatting and small spatial noise.

However, for some dense biological tissues which may have non-stationary noise with more detailed morphological features, the simple step of averaging B-scan images shown in the step 405 may smooth out the details of the morphological features. In addition, dense tissues have much stronger scattering and much larger spatial noises (mainly speckle noises), the spatial variation in the received signal caused by the noise may be comparable or even larger than that caused by the morphological structures to be detected. Therefore, new embodiment of the method shown in FIG. 2 may be needed.

Figure 7:
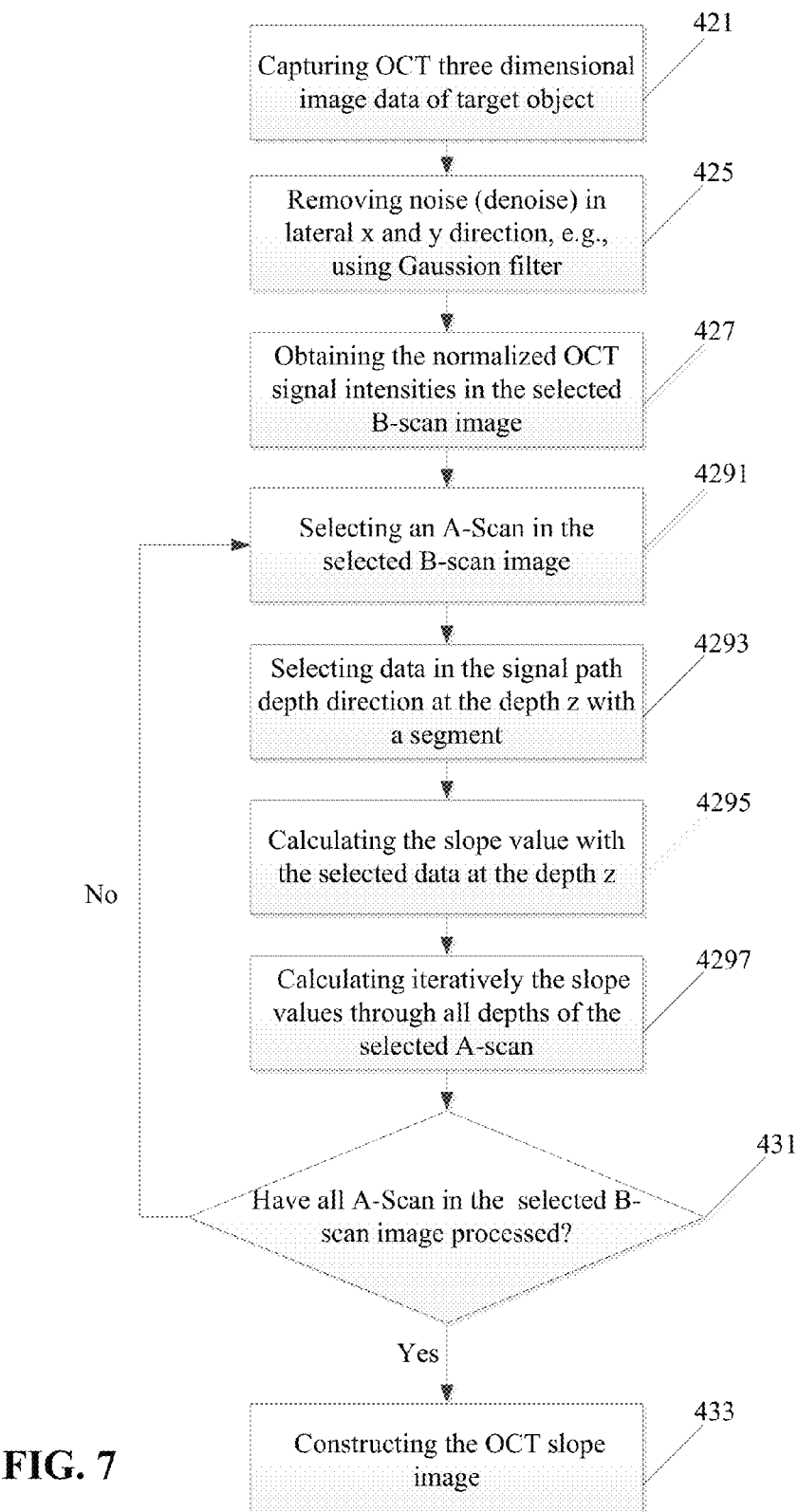
FIG. 7 shows another exemplary flow chart of a method for obtaining an OCT slope image by curve fitting after removing noise.

FIG. 7 shows another exemplary embodiment method for calculating an OCT slope image by curve fitting, within the framework of the general method shown in FIG. 2. The method can be applied to OCT images of dense biological tissues. The method can be applied to other OCT images as well. The method can be applied to the target object 123 placed in the OCT system 100 as shown in FIG. 1. The OCT system 100 may scan the reference path 115 and the signal path 117 in the interferometer 112, where the target object 123 is located at one end of the signal path 117. The method can be applied to other OCT systems as well.

At the step 421, 3-dimensional image information of the target object 123 may be captured by the OCT system. The 3-dimensional image information of the target object 123 may be captured by similar steps shown in the step 301 and the step 303 of FIG. 3, or by a similar step 401 shown in FIG. 4. For example, 3-dimensional image information of the target object 123 may be obtained at different locations and at different depths with different z coordinates below a surface of the target object 123.

At the step 425, a B-scan image may be selected among the different OCT images of the target object under different reference path lengths at different locations shifted in position represented by x and y coordinates. Operations may be performed to remove noise in the selected B-scan image to obtain a denoised B-scan image, which may have reduced spatial noise. Compared to the step 405 shown in FIG. 4, the step 425 is more general in the sense that "obtaining an average B-scan image" at the step 405 is just one possible way to remove the noise. Other more general operations may be used in addition to taking the average of B-scan images. There may be one single operation to remove the noise, there may be multiple operations to remove the noise. For example, a Gaussian filter may be used on the B-scan image to remove the noise. The Gaussian filter may have a size of 15 pixels×15 pixels and a standard deviation of 1. Other sizes of Gaussian filter or other filters may be used as well to remove the noise. The step 425 may be performed for each B-scan image of the target object, one B-scan image is selected at a time to remove the noise.

An example of the effect of removing noise in a B-scan image at the step 425 is shown in FIGS. 8A and 8B. Comparing the original B-scan image shown in FIG. 8A, and the denoised OCT B-scan image shown in FIG. 8B after the noise is removed, one can see that the salt noise is greatly reduced and the morphology structure information become more clear in FIG. 8B.

At the step 427, after the noise is removed from each B-scan image at the step 425, a normalized OCT image intensity may be obtained on the denoised B-scan images by dividing a signal intensity of the denoised B-scan image at each position represented by x and y coordinates by a signal intensity at a surface of the target object.

Figure 8C:
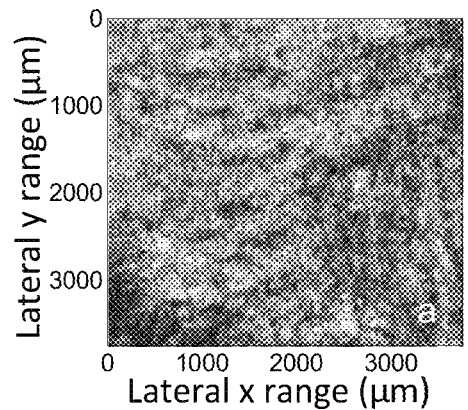
Figure 8C:
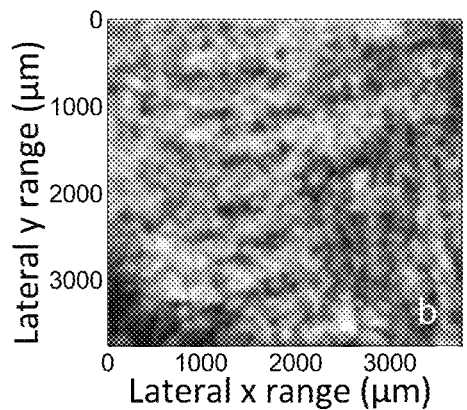
Figure 8C:
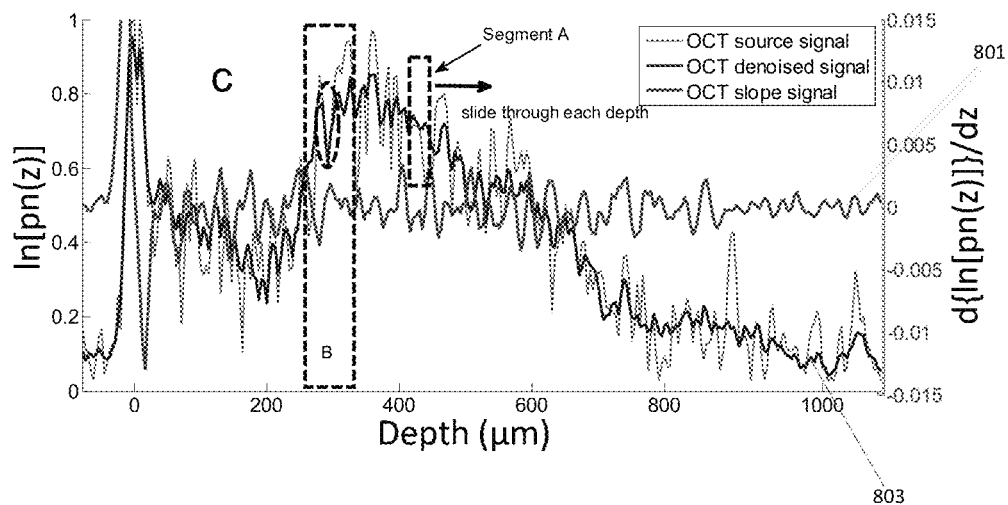

The next few steps from the step 4291 to the step 4297 are an alternative to the step 4091 and the step 4093 in FIG. 4, which are both refinement steps of the step 309 in FIG. 3. The general idea for the steps 4291 to 4297 is to avoid taking straightforward derivative operation on the data in the signal path direction, because noise spikes can introduce large derivative values. To further reduce the influences from the remaining noises at the denoised B-scan images, the coordinate z is divided into multiple segments, each segment has a subset of denoised B-scan images. An example is shown in FIG. 8C, where a plurality of denoised B-scan images are within a rectangle A which is a segment along the z-coordinate. Derivatives are taken for denoised B-scan images within each segment such as the ones within the rectangle A shown in FIG. 8C. More descriptions are given for each step from the step 4291 to the step 4297.

At the step 4291, an A-scan signal of a point at the denoised B-scan image with normalized OCT image intensity is selected. The selected A-scan signal comprises data along the z coordinate of the point at the denoised B-scan image.

At the step 4293, the signal path length is divided along the z coordinate into a plurality of smaller segments. The segments may be of equal length, or of different lengths. For each segment containing a depth z, data of the A-scan signal in the signal depth within the segment, such as the data shown in the rectangle A of FIG. 8C, may be used to obtain the derivative in the next step.

At the step 4295, a derivative of the A-scan signal in the segment with the selected data at the segment containing the depth z is calculated. A linear curve fitting may be performed to obtain the derivative or slope value of the denoised B-scan image in the segment containing the depth z.

The width of segment may impact the calculated slope value. The smaller the segment depth may be, the lesser impact the noise can have on the slope value, however, at the same time lesser spatial resolution. In the example, a depth of n=5 pixels may be chosen corresponding to a spatial resolution of about 20 μm.

Although there are many noisy variations in the denoised OCT data which may otherwise result in spiky derivatives, the slope curve obtained using the curve-fitting method in each segment can actually avoid such noisy spikes. As shown by the curve 801 and the curve 803 in FIG. 8C, one can see that the large signal decay in the A-scan data is removed in the slope data. In addition, as shown in box B, the curve-fitting operation for obtaining the OCT slope curve in a segment is effective in suppressing noisy spikes still remaining.

At the step 4297, derivatives of the A-scan signal are calculated through all segments in the signal path. This may be illustrated in FIG. 8C as the segment A slides through the coordinate z to obtain the slope curve 801 for each denoised A-scan curve 803.

In addition, at step 431, similar derivatives with respect to the signal path length through all positions of the averaged B-scan image are iteratively calculated.

At step 433, an OCT slope image having improved image information of the target object is constructed from the derivatives with respect to the signal path length through all positions of the averaged B-scan image.

Figure 9A:
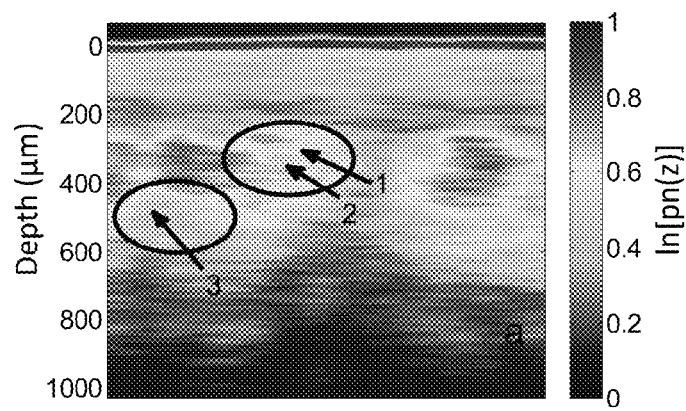
FIGS. 9A-9C show an exemplary comparison of an OCT image with noise removed, and a corresponding OCT slope image and its positive OCT slope image.
Figure 9B:
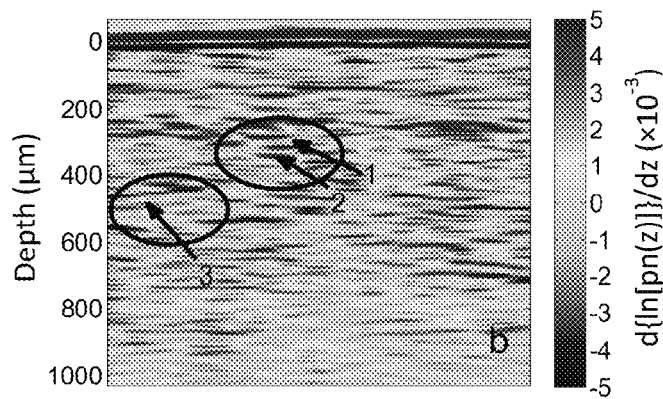
Figure 9C:
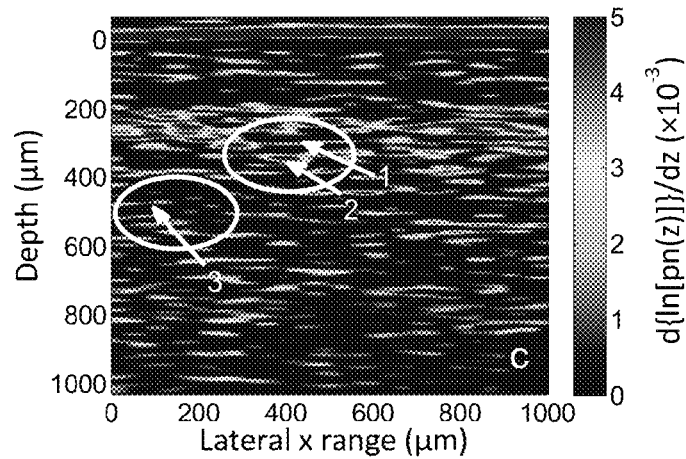

FIGS. 9A-9C demonstrate the result of applying the method shown in FIG. 7 to a section of in-vivo forearm skin tissue. Because collagen fiber bundles of a skin are the main components of the dermis and the predominant source of the scattering of skin, the skin is regarded as a dense tissue. In their nature states, the collagen fiber bundles have different diameters varying from 10 to 40 microns, and are aggregated into thick bundles which are arranged nearly parallel to the skin surface. The collagen fiber bundles can introduce variations of morphology structures in skin.

As shown in FIG. 9A, an OCT image of a skin sample may be obtained using a similar OCT system as described before. Note that FIGS. 9B and 9C are OCT slope images obtained by applying the method shown in FIG. 7. FIG. 9C is obtained by using both positive and negative slopes, while FIG. 9B is obtained by using only the positive slopes.

At a depth from 0 to 0.2 mm from the skin surface, all images FIGS. 9A-9C show similar morphological features, although the slope images FIGS. 9B and 9C have much better contrast. Those features resemble the collagen fiber bundles, consistent with the skin tissue. At a depth of more than 0.8 mm, the original OCT image shows almost no features at all due largely to the exponential signal decay. In contrast, the slope images FIGS. 9B and 9C can still clearly show detailed morphological structures expected from collagen fiber bundles. In the region between 0.2 to 0.4 mm, some features in the original image are blurred and mixed together, as indicated by arrows 1 and 2. However, in the slope images they are well defined and separated. Some shadowed features beneath the strong scattering structures indicated by arrow 3 are enhanced and become clear in the slope images. The slope image can effectively enhance the obscured features caused by the signal decay and the shadow effect in the original OCT image. It can also separate out features with overlaps to show more morphological details.

Figure 10:
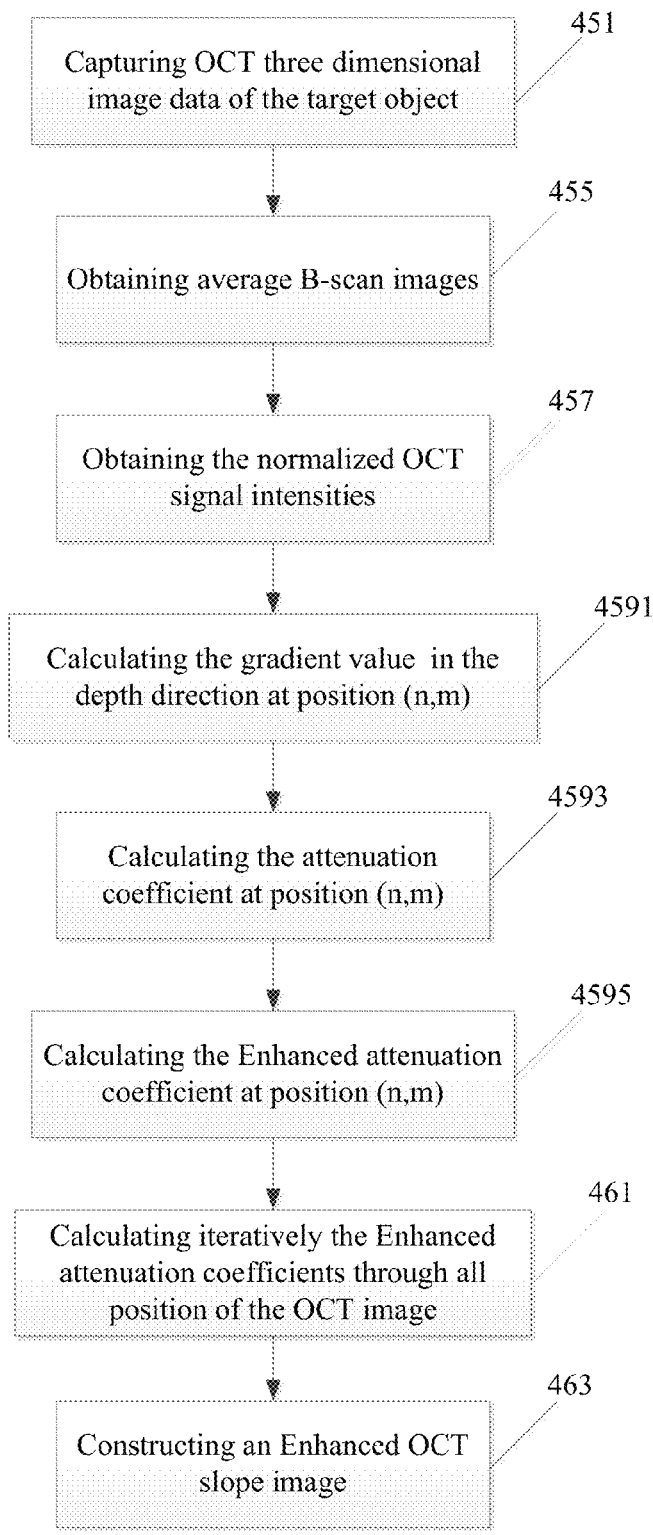
FIG. 10 shows another exemplary flow chart of a method for obtaining an enhanced OCT slope image.

FIG. 10 shows yet another exemplary embodiment method for calculating an OCT slope image. The method shown in FIG. 10 is based on another calculation related to the derivatives. Before the detailed steps of the method are presented, some analysis of OCT image signal may be useful to understand the method.

According to Beer-Lambert law, an OCT signal is given as $I_n(z)=I(z)/I_0=\exp(-2\mu_t z)$, where $I_0$ and $I(z)$ are the OCT signal intensity at the surface of the target object and at a depth z beneath the surface, $I_n(z)$ is the normalized OCT signal intensity, and $\mu_t$ is the attenuation coefficient of target object. Therefore, the normalized OCT signal intensity decays exponentially at a rate equal to twice the attenuation coefficient of the target object. Generally, the change of the inner structure induces a variation of the attenuation coefficient, therefore the attenuation coefficient can be used to indicate the inner structure. The attenuation coefficient can be described as a derivative $\mu_t(z)=-\frac{1}{2}d\{\ln[I_n(z)]\}/dz$.

In the actual discrete calculation of the slope values of each OCT A-scan, the attenuation coefficient can be described as $$\mu_t(n) = -\frac{1}{2}\left[\frac{\ln[I_n(n+1)] - \ln[I_n(n)]}{\delta z}\right],$$

where $\ln[I_n(n)]$ is the nth logarithm value of an OCT A-scan, and $\delta z$ is the actual distance of one pixel.

For further enhancing the deep features of the target object, the slope values of the original OCT A-scan can be divided by the original OCT A-scan value to obtain the enhanced attenuation coefficient $E\mu_t(z)$, where $$E\mu_t(z) = -\frac{1}{2}\frac{\frac{d\{\ln[I_n(z)]\}}{dz}}{\ln[I_n(z)]},$$

$I_n(z)$ is the denominator of the formula, and $1/I_n(z)$ is the enhancing factor. $E\mu_t(z)$ reflects the relative change of attenuation coefficient to the current OCT signal intensity in the depth z, which may be a relative attenuation coefficient. In the discrete way, it can be described as $$E\mu_t(n) = -\frac{1}{2}\left[\frac{\ln[I_n(n+1)] - \ln[I_n(n)]}{\ln[I_n(n)]\delta z}\right].$$

When the image depth increases, the depth value of n increases, resulting in reduced value of $I_n(z)$, which in turn leads to increased value of $1/I_n(z)$, so it can effectively compensates the influence of the attenuation.

Based on the above analysis, the method shown in FIG. 10 is described below. The method can be applied to the target object 123 placed in the OCT system 100 as shown in FIG. 1. The OCT system 100 may scan the reference path 115 and the signal path 117 in the interferometer 112, where the target object 123 is located at one end of the signal path 117. The method can be applied to other OCT systems as well.

At the step 451, 3-dimensional image information of the target object 123 may be captured by the OCT system. The 3-dimensional image information of the target object 123 may be captured by similar steps shown in the step 301 and the step 303 of FIG. 3, or by a similar step 401 shown in FIG. 4. For example, 3-dimensional image information of the target object 123 may be obtained at different locations and at different depths with different z coordinates below a surface of the target object 123.

At the step 455, an averaged B-scan image at different z coordinate below a surface of the target object 123 is obtained. For example, the averaged B-scan image may be obtained by averaging 20 consecutive B-scan images to suppress the influence of speckle noise. There may be other number of consecutive B-scan images to be averaged instead of 20. The exact number of consecutive B-scan images to be averaged depends on the OCT system, the target object, and other factors affecting the performance. There may be other ways to remove noises instead of taking an average of consecutive B-scan images.

At the step 457, a normalized OCT image intensity $I_n(n,m)$ may be obtained by dividing a signal intensity $I(n,m)$ of an averaged B-scan image at each position represented by x and y coordinates by a signal intensity $I_0(m)$ at a surface of the target object 123.

At the step 4591 a gradient value $G(n,m)$ of the normalized OCT image intensity in the signal path length direction is obtained by subtracting an OCT signal intensity in a next depth $I(n+1,m)$ to the OCT signal intensity $I(n,m)$ as $G(n,m) = \ln [I_n(n+1,m)] - \ln [I_n(n,m)]$.

At the step 4593, an attenuation coefficient $\mu_t(n,m)$ may be calculated by dividing the gradient value $G(n,m)$ by a double actual distance of one pixel and then multiplying −1, which is effectively a derivative, $$\mu_t(n, m) = -\frac{G(n, m)}{2\delta z}.$$

At the step 4595, an enhanced attenuation coefficient $E\mu_t(n,m)$ may be obtained by dividing the attenuation coefficient $\mu_t(n,m)$ by the normalized OCT image intensity $I_n(n,m)$, $$E\mu_t(n, m) = \frac{\mu_t(n, m)}{\ln(I_n(n, m))}.$$

In addition, at the step 461, similar enhanced attenuation coefficients through all positions of the averaged B-scan image are iteratively calculated.

Finally, at the step 463, an enhanced OCT slope image is constructed to have improved image information of the target object from the enhanced attenuation coefficients through all position of the averaged B-scan image.

The method described above is applied to the artifact shown in FIG. 11A, which is a multi-layer adhesive tape. An enhanced OCT slope images are obtained and shown in FIGS. 11B and 11C. One can observe that the layer structures are effectively enhanced in the enhanced OCT slope images FIGS. 11B and 11C, especially the layer information in the deeper layers.

Another example is further tested, where an artifact comprises multi-layer tapes with inside slots filled with silica powder, little fiber segment and carbon dust to make multi-scattering. The OCT image of the artifact is shown in FIG. 12A. One can see that the layer structure in the artifact becomes clear in FIG. 12C, which is an enhanced OCT slope image.

The above examples provide implementations that use the OCT slope image to enhance the visualization of morphology structures by suppressing the influences of the optical decay, the shadowing effect, and the multiple photon scattering effect.

Implementations of the subject matter and the functional operations described in this document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for extracting image information from images of a target object in an optical coherence tomography (OCT) device obtained via scanning a reference path length relative to a signal path length of a signal path in the interferometer of the OCT device where the target object is located at one end of the signal path, comprising:
    obtaining different OCT images of the target object under different reference path lengths;
    processing the different OCT images to obtain a derivative with respect to the signal path length of image information of the different images; and
    processing the derivative to extract improved image information of the target object to reduce an effect of a signal decay due to scattering of light in the target object,
    wherein obtaining different OCT images of the target object under different reference path lengths comprises:
        obtaining different OCT images of the target object at different locations shifted in position represented by x and y coordinates along a direction substantially perpendicular to a direction of incidence of light into the target object represented by z coordinate; and
        obtaining different OCT images of the target object at different reference path lengths at each of the different locations to obtain 3-dimensional image information of the target object at the different locations and at different depths with different z coordinate below a surface of the target object, and
    wherein processing the different OCT images to obtain a derivative with respect to the signal path length of image information of the different images comprises:
        averaging a first number of consecutive B-scan images among the different OCT images to obtain an averaged B-scan image;
        obtaining a normalized OCT image intensity of a position in the averaged B-scan image by dividing a signal intensity of the position in the averaged B-scan image by a signal intensity at a surface of the target object;
        calculating a gradient value of the normalized OCT image intensity in the signal path length direction by subtracting a normalized OCT image intensity in a next depth to the normalized OCT image intensity; and
        obtaining the derivative with respect to the signal path length by dividing the gradient value of the normalized OCT image intensity by double actual distance of one pixel.

2. The method of claim 1, wherein processing the derivative to extract improved image information of the target object comprises:
    iteratively calculating derivatives with respect to the signal path length through all positions of the averaged B-scan image; and
    reconstructing an OCT slope image having improved image information of the target object from the derivatives with respect to the signal path length through all positions of the averaged B-scan image.

3. A method for extracting image information from images of a target object in an optical coherence tomography (OCT) device obtained via scanning a reference path length relative to a signal path length of a signal path in the interferometer of the OCT device where the target object is located at one end of the signal path, comprising:

obtaining different OCT images of the target object under different reference path lengths;

processing the different OCT images to obtain a derivative with respect to the signal path length of image information of the different images; and processing the derivative to extract improved image information of the target object to reduce an effect of a signal decay due to scattering of light in the target object, wherein obtaining different OCT images of the target object under different reference path lengths comprises:

obtaining different OCT images of the target object at different locations shifted in position represented by x and y coordinates along a direction substantially perpendicular to a direction of incidence of light into the target object represented by z coordinate; and obtaining different OCT images of the target object at different reference path lengths at each of the different locations to obtain 3-dimensional image information of the target object at the different locations and at different depths with different z coordinate below a surface of the target object, and wherein processing the different OCT images to obtain a derivative with respect to the signal path length of image information of the different images comprises:

selecting a B-scan image among the different OCT images of the target object under different reference path lengths at different locations shifted in position represented by x and y coordinates;

removing noise in the selected B-scan image to obtain a denoised B-scan image;

obtaining a normalized OCT image intensity by dividing a signal intensity of the denoised B-scan image at each position represented by x and y coordinates by a signal intensity at a surface of the target object;

selecting an A-scan signal of a point at the denoised B-scan image with normalized OCT image intensity;

dividing the signal path length into a plurality of smaller segments;

selecting data of the A-scan signal in the signal depth direction at a segment containing a depth z;

calculating the derivative of the A-scan signal in the segment with the selected data at the segment containing the depth z; and calculating iteratively derivatives of the A-scan signal through all segments in the signal path.

4. The method of 3, wherein removing noise in the selected B-scan image to obtain the denoised B-scan image comprises:

removing noise in the selected B-scan image by a Gaussian filter to obtain the denoised B-scan image.

5. The method of 4, wherein the Gaussian filter has a size of 15 pixels×15 pixels and a standard deviation of 1.

6. The method of claim 3, wherein the plurality of smaller segments of the signal path length has a length of 5 pixels.

7. A method for extracting image information from images of a target object in an optical coherence tomography (OCT) device obtained via scanning a reference path length relative to a signal path length of a signal path in the interferometer of the OCT device where the target object is located at one end of the signal path, comprising:

obtaining different OCT images of the target object under different reference path lengths;

processing the different OCT images to obtain a derivative with respect to the signal path length of image information of the different images; and processing the derivative to extract improved image information of the target object to reduce an effect of a signal decay due to scattering of light in the target object, wherein obtaining different OCT images of the target object under different reference path lengths comprises:

obtaining different OCT images of the target object at different locations shifted in position represented by x and y coordinates along a direction substantially perpendicular to a direction of incidence of light into the target object represented by z coordinate; and obtaining different OCT images of the target object at different reference path lengths at each of the different locations to obtain 3-dimensional image information of the target object at the different locations and at different depths with different z coordinate below a surface of the target object, and wherein processing the different OCT images to obtain a derivative with respect to the signal path length of image information of the different images comprises:

averaging a first number of consecutive B-scan images among the different OCT images to obtain an averaged B-scan image;

obtaining a normalized OCT image intensity in the averaged B-scan image by dividing a signal intensity of an averaged B-scan image at each position represented by x and y coordinates by a signal intensity at a surface of the target object;

obtaining a gradient value of the normalized OCT image intensity in the signal path length direction by subtracting an OCT signal intensity in a next depth to the OCT signal intensity;

calculating an attenuation coefficient by dividing the gradient value by double actual distance of one pixel and then multiplying −1; and obtaining an enhanced attenuation coefficient by dividing the attenuation coefficient by the normalized OCT image intensity.

8. The method of claim 7, wherein processing the derivative to extract improved image information of the target object comprises:

iteratively calculating enhanced attenuation coefficients through all position of the averaged B-scan image; and reconstructing an enhanced OCT slope image having improved image information of the target object from the enhanced attenuation coefficients through all position of the averaged B-scan image.

9. A method for extracting image information from images of a target object in an optical coherence tomography (OCT) device obtained via scanning a reference path length relative to a signal path length of a signal path in the interferometer of the OCT device where the target object is located at one end of the signal path, comprising:

obtaining different OCT images of the target object under different reference path lengths;

processing the different OCT images to obtain a derivative with respect to the signal path length of image information of the different images; and processing the derivative to extract improved image information of the target object to enhance image information of boundaries of heterogeneous layers in the target object, wherein obtaining different OCT images of the target object under different reference path lengths comprises:

obtaining different OCT images of the target object at different locations shifted in position represented by x and y coordinates along a direction substantially perpendicular to a direction of incidence of light into the target object represented by z coordinate; and obtaining different OCT images of the target object at different reference path lengths at each of the different locations to obtain 3-dimensional image information of the target object at the different locations and at different depths with different z coordinate below a surface of the target object, wherein processing the different OCT images to obtain a derivative with respect to the signal path length of image information of the different images comprises:

averaging a first number of consecutive B-scan images among the different OCT images to obtain an averaged B-scan image;

obtaining a normalized OCT image intensity of a position in the averaged B-scan image by dividing a signal intensity of the position in the averaged B-scan image by a signal intensity at a surface of the target object;

calculating a gradient value of the normalized OCT image intensity in the signal path length direction by subtracting a normalized OCT image intensity in a next depth to the normalized OCT image intensity; and obtaining the derivative with respect to the signal path length by dividing the gradient value of the normalized OCT image intensity by double actual distance of one pixel.

10. A method for extracting image information from images of a target object in an optical coherence tomography (OCT) device obtained via scanning a reference path length relative to a signal path length of a signal path in the interferometer of the OCT device where the target object is located at one end of the signal path, comprising:

obtaining different OCT images of the target object under different reference path lengths;

processing the different OCT images to obtain a derivative with respect to the signal path length of image information of the different images; and processing the derivative to extract improved image information of the target object to enhance image information of boundaries of heterogeneous layers in the target object, wherein obtaining different OCT images of the target object under different reference path lengths comprises:

obtaining different OCT images of the target object at different locations shifted in position represented by x and y coordinates along a direction substantially perpendicular to a direction of incidence of light into the target object represented by z coordinate; and obtaining different OCT images of the target object at different reference path lengths at each of the different locations to obtain 3-dimensional image information of the target object at the different locations and at different depths with different z coordinate below a surface of the target object, wherein processing the different OCT images to obtain a derivative with respect to the signal path length of image information of the different images comprises:

selecting a B-scan image among the different OCT images of the target object under different reference path lengths at different locations shifted in position represented by x and y coordinates;

removing noise in the selected B-scan image to obtain a denoised B-scan image;

obtaining a normalized OCT image intensity by dividing a signal intensity of the denoised B-scan image at each position represented by x and y coordinates by a signal intensity at a surface of the target object;

selecting an A-scan signal of a point at the denoised B-scan image with normalized OCT image intensity;

dividing the signal path length into a plurality of smaller segments;

selecting data of the A-scan signal in the signal depth direction at a segment containing a depth z;

calculating the derivative of the A-scan signal in the segment with the selected data at the segment containing the depth z; and calculating iteratively derivatives of the A-scan signal through all segments in the signal path.

11. A method for extracting image information from images of a target object in an optical coherence tomography (OCT) device obtained via scanning a reference path length relative to a signal path length of a signal path in the interferometer of the OCT device where the target object is located at one end of the signal path, comprising:

obtaining different OCT images of the target object under different reference path lengths;

processing the different OCT images to obtain a derivative with respect to the signal path length of image information of the different images; and processing the derivative to extract improved image information of the target object to enhance image information of boundaries of heterogeneous layers in the target object, wherein obtaining different OCT images of the target object under different reference path lengths comprises:

obtaining different OCT images of the target object at different locations shifted in position represented by x and y coordinates along a direction substantially perpendicular to a direction of incidence of light into the target object represented by z coordinate; and obtaining different OCT images of the target object at different reference path lengths at each of the different locations to obtain 3-dimensional image information of the target object at the different locations and at different depths with different z coordinate below a surface of the target object, wherein processing the different OCT images to obtain a derivative with respect to the signal path length of image information of the different images comprises:

averaging a first number of consecutive B-scan images among the different OCT images to obtain an averaged B-scan image;

obtaining a normalized OCT image intensity in the averaged B-scan image by dividing a signal intensity of an averaged B-scan image at each position represented by x and y coordinates by a signal intensity at a surface of the target object;

obtaining a gradient value of the normalized OCT image intensity in the signal path length direction by subtracting an OCT signal intensity in a next depth to the OCT signal intensity;

calculating an attenuation coefficient by dividing the gradient value by double actual distance of one pixel and then multiplying −1; and obtaining an enhanced attenuation coefficient by dividing the attenuation coefficient by the normalized OCT image intensity.

12. A method for extracting image information from images of a target object in an optical coherence tomography (OCT) device obtained via scanning a reference path length relative to a signal path length of a signal path in the interferometer of the OCT device where the target object is located at one end of the signal path, comprising:

obtaining different OCT images of the target object (1) at different locations shifted in position represented by x and y coordinates along a direction substantially perpendicular to a direction of incidence of light into the target object represented by z coordinate, and (2) at different reference path lengths at each of the different locations to obtain 3-dimensional image information of the target object at the different locations and at different depths with different z coordinates below a surface of the target object;

processing OCT images of the target object obtained at different locations shifted in position represented by x and y coordinates to obtain an averaged B-scan image;

obtaining a normalized OCT image intensity by dividing a signal intensity of an averaged B-scan image at each position represented by x and y coordinates by a signal intensity at a surface of the target object;

obtaining a gradient value of the normalized OCT image intensity with respect to the z coordinate; and using gradient values of the normalized OCT image intensities at different locations to construct an OCT slope image of the target image.

13. The method of claim 12, wherein obtaining a gradient value of the normalized OCT image intensity with respect to the z coordinate comprises:

calculating the gradient value of the normalized OCT image intensity by subtracting a normalized OCT image intensity in a next depth to the normalized OCT image intensity.

14. An optical coherence tomography (OCT) device, comprising:

an optical interferometer having a signal path in which a target object is located to receive light of a signal beam and a reference path for carrying a reference light beam to cause a spatial overlap the reflected or back scattered signal light from the target object and the reference light beam to produce an OCT optical signal beam containing different OCT images of the target object that are obtained (1) at different locations shifted in position represented by x and y coordinates along a direction substantially perpendicular to a direction of incidence of light into the target object represented by z coordinates in the signal path, and (2) at different reference path lengths of the reference path at each of the different locations to obtain 3-dimensional image information of the target object at the different locations and at different depths with different z coordinates below a surface of the target object; and an imaging processing device which processes the OCT images of the target object obtained at different locations shifted in position represented by x and y coordinates to obtain an averaged B-scan image, obtains a normalized OCT image intensity by dividing a signal intensity of an averaged B-scan OCT image at each position represented by x and y coordinates by a signal intensity at a surface of the target object, obtains a gradient value of the normalized OCT image intensity with respect to the z coordinate, and uses gradient values of the normalized OCT image intensities at different at different locations to construct an OCT slope image of the target image.

15. The OCT device of claim 14, wherein the image processing device obtaining a gradient value of the normalized OCT image intensity with respect to the z coordinate comprises:

calculating the gradient value of the normalized OCT image intensity with respect to the z coordinate by subtracting a normalized OCT image intensity in a next depth to the normalized OCT image intensity.

16. The OCT device of claim 15, wherein the image processing device using gradient values of the normalized OCT image intensities at different at different locations to construct an OCT slope image of the target image comprises:

obtaining a derivative with respect to the signal path length by dividing the gradient value of the normalized OCT image intensity by double actual distance of one pixel;

iteratively calculating derivatives with respect to the signal path length through all positions of the averaged B-scan image; and reconstructing the OCT slope image having improved image information of the target object from the derivatives with respect to the signal path length through all positions of the averaged B-scan image.

17. An optical coherence tomography (OCT) device, comprising:

an optical interferometer having a signal path in which a target object is located to receive light of a signal beam and a reference path for carrying a reference light beam to cause a spatial overlap the reflected or back scattered signal light from the target object and the reference light beam to produce an OCT optical signal beam containing different OCT images of the target object that are obtained (1) at different locations shifted in position represented by x and y coordinates along a direction substantially perpendicular to a direction of incidence of light into the target object represented by z coordinates in the signal path, and (2) at different reference path lengths of the reference path at each of the different locations to obtain 3-dimensional image information of the target object at the different locations and at different depths with different z coordinates below a surface of the target object; and an imaging processing device which:

selects a B-scan image among the different OCT images of the target object under different reference path lengths at different locations shifted in position represented by x and y coordinates;

removes noise in the selected B-scan image to obtain a denoised B-scan image;

obtains a normalized OCT image intensity by dividing a signal intensity of the denoised B-scan image at each position represented by x and y coordinates by a signal intensity at a surface of the target object;

selects an A-scan signal of a point at the denoised B-scan image with normalized OCT image intensity;

divides the signal path length into a plurality of smaller segments;

selects data of the A-scan signal in the signal depth direction at a segment containing a depth z;

calculates a derivative of the A-scan signal in the segment with the selected data at the segment containing the depth z;

calculates iteratively derivatives of the A-scan signal through all segments in the signal path;

calculates iteratively derivatives with respect to the signal path length through all positions of the denoised B-scan image; and reconstructs an OCT slope image having improved image information of the target object from the derivatives with respect to the signal path length through all positions of the denoised B-scan image.

18. The OCT device of 17, wherein removing noise in the selected B-scan image to obtain the denoised B-scan image comprises:
removing noise in the selected B-scan image by a Gaussian filter to obtain the denoised B-scan image.

19. The OCT device of 17, wherein removing noise in the selected B-scan image to obtain the denoised B-scan image comprises:
removing noise in the selected B-scan image by averaging a first number of consecutive B-scan images among the different OCT images to obtain an averaged B-scan image.

20. An optical coherence tomography (OCT) device, comprising:
an optical interferometer having a signal path in which a target object is located to receive light of a signal beam and a reference path for carrying a reference light beam to cause a spatial overlap the reflected or back scattered signal light from the target object and the reference light beam to produce an OCT optical signal beam containing different OCT images of the target object that are obtained (1) at different locations shifted in position represented by x and y coordinates along a direction substantially perpendicular to a direction of incidence of light into the target object represented by z coordinates in the signal path, and (2) at different reference path lengths of the reference path at each of the different locations to obtain 3-dimensional image information of the target object at the different locations and at different depths with different z coordinates below a surface of the target object; and
an imaging processing device which:
averages a first number of consecutive B-scan images among the different OCT images to obtain an averaged B-scan image;
obtains a normalized OCT image intensity in the averaged B-scan image by dividing a signal intensity of the averaged B-scan image at each position represented by x and y coordinates by a signal intensity at a surface of the target object;
obtains a gradient value of the normalized OCT image intensity in the signal path length direction;
obtains an attenuation coefficient from the gradient value;
obtains an enhanced attenuation coefficient by dividing the attenuation coefficient by the normalized OCT image intensity;
iteratively calculates enhanced attenuation coefficients through all position of the averaged B-scan image; and
reconstructs an enhanced OCT slope image having improved image information of the target object from the enhanced attenuation coefficients through all position of the averaged B-scan image.

21. The OCT device of 20, wherein obtaining a gradient value of the normalized OCT image intensity in the signal path length direction comprises:
obtaining a gradient value of the normalized OCT image intensity in the signal path length direction by subtracting an OCT signal intensity in a next depth to the OCT signal intensity.

22. The OCT device of 20, wherein obtaining an attenuation coefficient from the gradient value comprises:
obtaining an attenuation coefficient from the gradient value by dividing the gradient value by double actual distance of one pixel and then multiplying −1.

23. An optical coherence tomography (OCT) device, comprising:
an optical interferometer having a signal path in which a target object is located to receive light of a signal beam and a reference path for carrying a reference light beam to cause a spatial overlap the reflected or back scattered signal light from the target object and the reference light beam to produce an OCT optical signal beam containing different OCT images of the target object at different locations shifted in position represented by x and y coordinates along a direction substantially perpendicular to a direction of incidence of light into the target object and at different z coordinates in the signal path to obtain 3-dimensional image information of the target object at the different x, y and z locations below a surface of the target object; and
an imaging processing device which processes the OCT images of the target object obtained at different locations shifted in position represented by x and y coordinates to obtain an averaged B-scan image, obtains a normalized OCT image intensity by dividing a signal intensity of an averaged B-scan OCT image at each position represented by x and y coordinates by a signal intensity at a surface of the target object, obtains a gradient value of the normalized OCT image intensity with respect to the z coordinate, and uses gradient values of the normalized OCT image intensities at different locations to construct an OCT slope image of the target image.

24. The OCT device of claim 23, wherein the image processing device obtaining a gradient value of the normalized OCT image intensity with respect to the z coordinate comprises:
calculating the gradient value of the normalized OCT image intensity with respect to the z coordinate by subtracting a normalized OCT image intensity in a next depth to the normalized OCT image intensity.

25. The OCT device of claim 23, wherein the image processing device using gradient values of the normalized OCT image intensities at different at different locations to construct an OCT slope image of the target image comprises:
obtaining a derivative with respect to the signal path length by dividing the gradient value of the normalized OCT image intensity by double actual distance of one pixel;
iteratively calculating derivatives with respect to the signal path length through all positions of the averaged B-scan image; and
reconstructing the OCT slope image having improved image information of the target object from the derivatives with respect to the signal path length through all positions of the averaged B-scan image.

26. The OCT device of claim 23, comprising:
a broadband light source that produces light for the signal beam and the reference light beam in the optical interferometer.

27. An optical coherence tomography (OCT) device, comprising:
an optical interferometer having a signal path in which a target object is located to receive light of a signal beam and a reference path for carrying a reference light beam to cause a spatial overlap the reflected or back scattered signal light from the target object and the reference light beam to produce an OCT optical signal beam containing different OCT images of the target object at different locations shifted in position represented by x and y coordinates along a direction substantially perpendicular to a direction of incidence of light into the target object and at different z coordinates in the signal path to obtain 3-dimensional image information of the target object at the different x, y and z locations below a surface of the target object; and an imaging processing device which:

averages a first number of consecutive B-scan images among the different OCT images to obtain an averaged B-scan image;

obtains a normalized OCT image intensity in the averaged B-scan image by dividing a signal intensity of the averaged B-scan image at each position represented by x and y coordinates by a signal intensity at a surface of the target object;

obtains a gradient value of the normalized OCT image intensity in the signal path length direction;

obtains an attenuation coefficient from the gradient value;

obtains an enhanced attenuation coefficient by dividing the attenuation coefficient by the normalized OCT image intensity;

iteratively calculates enhanced attenuation coefficients through all position of the averaged B-scan image; and reconstructs an enhanced OCT slope image having improved image information of the target object from the enhanced attenuation coefficients through all position of the averaged B-scan image.

28. The OCT device of 27, wherein obtaining a gradient value of the normalized OCT image intensity in the signal path length direction comprises:

obtaining a gradient value of the normalized OCT image intensity in the signal path length direction by subtracting an OCT signal intensity in a next depth to the OCT signal intensity.

29. The OCT device of claim 27, comprising:

a broadband light source that produces light for the signal beam and the reference light beam in the optical interferometer.

30. A method for extracting image information from images of a target object in an optical coherence tomography (OCT) device, comprising:

obtaining different OCT images of the target object at different depths into the target object;

processing the different OCT images to obtain a derivative with respect to the depth of image information of the different OCT images; and processing the derivative to extract improved image information of the target object to reduce an effect of a signal decay due to scattering of light in the target object, wherein obtaining different OCT images of the target object at different depths into the target object comprises:

obtaining different OCT images of the target object at different locations shifted in position represented by x and y coordinates along a direction substantially perpendicular to a direction of incidence of light into the target object represented by z coordinate; and obtaining different OCT images of the target object at different z coordinates at each of the different x and y locations to obtain 3-dimensional image information of the target object at the different locations and at different depths below a surface of the target object, and wherein processing the different OCT images to obtain a derivative with respect to the signal path length of image information of the different images comprises:

averaging a first number of consecutive B-scan images among the different OCT images to obtain an averaged B-scan image;

obtaining a normalized OCT image intensity of a position in the averaged B-scan image by dividing a signal intensity of the position in the averaged B-scan image by a signal intensity at a surface of the target object;

calculating a gradient value of the normalized OCT image intensity in the signal path length direction by subtracting a normalized OCT image intensity in a next depth to the normalized OCT image intensity; and obtaining the derivative with respect to the signal path length by dividing the gradient value of the normalized OCT image intensity by double actual distance of one pixel.

31. The method of claim 30, wherein processing the derivative to extract improved image information of the target object comprises:

iteratively calculating derivatives with respect to the signal path length through all positions of the averaged B-scan image; and reconstructing an OCT slope image having improved image information of the target object from the derivatives with respect to the signal path length through all positions of the averaged B-scan image.

32. The method of claim 30, wherein processing the different OCT images to obtain a derivative with respect to the signal path length of image information of the different OCT images comprises:

selecting a B-scan image among the different OCT images of the target object under different reference path lengths at different locations shifted in position represented by x and y coordinates;

removing noise in the selected B-scan image to obtain a denoised B-scan image;

obtaining a normalized OCT image intensity by dividing a signal intensity of the denoised B-scan image at each position represented by x and y coordinates by a signal intensity at a surface of the target object;

selecting an A-scan signal of a point at the denoised B-scan image with normalized OCT image intensity;

dividing the signal path length into a plurality of smaller segments;

selecting data of the A-scan signal in the signal depth direction at a segment containing a depth z;

calculating the derivative of the A-scan signal in the segment with the selected data at the segment containing the depth z; and calculating iteratively derivatives of the A-scan signal through all segments in the signal path.

33. The method of 32, wherein removing noise in the selected B-scan image to obtain the denoised B-scan image comprises:

removing noise in the selected B-scan image by a Gaussian filter to obtain the denoised B-scan image.

34. The method of claim 30, comprising:
using a broadband light source to produce light that is used to obtain the different OCT images of the target object.

* * * * *